US010758201B2

(12) United States Patent
Lin et al.

(10) Patent No.: US 10,758,201 B2
(45) Date of Patent: *Sep. 1, 2020

(54) VARIANCE REDUCTION FOR MONTE CARLO-BASED SCATTER ESTIMATION

(71) Applicant: CARESTREAM HEALTH, INC., Rochester, NY (US)

(72) Inventors: Yuan Lin, Rochester, NY (US); William J. Sehnert, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 161 days.

This patent is subject to a terminal disclaimer.

(21) Appl. No.: 16/106,718

(22) Filed: Aug. 21, 2018

(65) Prior Publication Data

US 2019/0175132 A1 Jun. 13, 2019

Related U.S. Application Data

(60) Provisional application No. 62/597,975, filed on Dec. 13, 2017.

(51) Int. Cl.
*G06T 11/00* (2006.01)
*G06K 9/00* (2006.01)
(Continued)

(52) U.S. Cl.
CPC ............ *A61B 6/5282* (2013.01); *A61B 6/483* (2013.01); *A61B 6/505* (2013.01); *A61B 6/583* (2013.01);
(Continued)

(58) Field of Classification Search
None
See application file for complete search history.

(56) References Cited

U.S. PATENT DOCUMENTS 6,256,367 B1 7/2001 Vartanian
2008/0095302 A1 4/2008 Ruhrnschopf et al.
(Continued)

FOREIGN PATENT DOCUMENTS

WO 2016/003957 1/2016

OTHER PUBLICATIONS

Michael Ljungberg et al., "Comparison of Four Scatter Correction Methods Using Monte Carlo Simulated Source Distributions," J. Nucl. Med., 1994; 35: pp. 143-151.
(Continued)

*Primary Examiner* — Randolph I Chu (57) ABSTRACT

A method rotates a radiation source and a detector over a sequence of acquisition angles about a subject and acquires, at each acquisition angle, a 2D projection image. A simulation subset is formed that contains some, but not all, of the acquired 2D projection images, wherein subset membership is determined according to relative signal change between successive 2D projection images. Scatter is characterized for the acquired sequence of projection images according to the formed simulation subset. One or more of the acquired sequence of projection images is corrected using the scatter characterization. An image volume is reconstructed and stored according to the sequence of scatter corrected projection images. One or more images of the reconstructed image volume are rendered to a display or transmitting the stored image volume data.

20 Claims, 8 Drawing Sheets

(51) Int. Cl.
*A61B 6/00* (2006.01)
*G01N 23/04* (2018.01)
(52) U.S. Cl.
CPC ....... *G01N 23/04* (2013.01); *G01N 2223/419* (2013.01); *G06T 11/005* (2013.01); *G06T 2207/10116* (2013.01)

(56) References Cited

U.S. PATENT DOCUMENTS

| | | | | |
|---|---|---|---|---|
| 2014/0218362 | A1* | 8/2014 | Gindele | G06T 11/006 345/424 |
| 2017/0086770 | A1* | 3/2017 | Morita | A61B 6/032 |
| 2019/0175132 | A1* | 6/2019 | Lin | A61B 6/483 |
| 2019/0175133 | A1* | 6/2019 | Lin | A61B 6/483 |

OTHER PUBLICATIONS

Michael Ljungberg, "Development and Evaluation of Attenuation and Scatter Correction Techniques for SPECT using the Monte Carlo Method," University of Lund, dissertation by Ljungberg, 1990, 63 pages.

Ernesto Mainegra-Hing et al., "Variance reduction techniques for fast Monte Carlo CBCT scatter correction calculations," Phys. Med. Biol. 55, 2010, pp. 4495-4507.

G. Poludniowski et al., "An efficient Monte Carlo-based algorithm for scatter correction in keV cone-beam CT," Physics in Medicine and Biology, 2009:54(12): 16 pages.

\* cited by examiner

VARIANCE REDUCTION FOR MONTE CARLO-BASED SCATTER ESTIMATION

CROSS REFERENCE TO RELATED APPLICATIONS

This application claims priority to U.S. Provisional application U.S. Ser. No. 62/597,975, provisionally filed on Dec. 13, 2017 entitled "VARIANCE REDUCTION FOR MONTE CARLO-BASED SCATTER ESTIMATION", in the names of LIN et al, incorporated herein in its entirety.

TECHNICAL FIELD

The disclosure relates generally to medical imaging and in particular to methods and apparatus for characterization and correction of scatter effects in X-ray images.

BACKGROUND

Various types of X-ray imaging offer tools for diagnostic assessment of patient health. Conventional x-ray imaging captures individual, two-dimensional (2D) images of patient anatomy. Volume imaging modalities obtain multiple images in sequence to provide additional depth information, allowing imaging of internal anatomy with three-dimensional (3D) views displayed from different angles and with adjustable sectioning for viewing slices of the volume data, thus allowing the view of internal structures and organs of the patient at different depths from the skin surface.

One known difficulty with X-ray imaging in both 2D imaging modalities (such as radiography, fluoroscopy, or mammography, and the like) and 3D imaging modalities (such as computed tomography CT, multi-detector computed tomography MDCT, cone beam computed tomography CBCT, tomosynthesis, dual energy CT, or spectral CT, and the like) relates to the adverse impact of accumulated effects of scattered radiation on image quality. Scatter itself results from secondary, randomized effects of interaction of the radiation energy with the irradiated tissue. Scatter occurs when radiation from the x-ray source reaches a detector by an indirect path that can extend into material that lies outside the field of view. The primary X-ray beam is directed towards and bombards the sample with some of the X-ray radiation being absorbed, a smaller amount being scattered, and the remainder continuing on to the detector. Scatter is known to contribute to noise and low contrast in the projection images and can substantially reduce image quality and introduce artifacts into the x-ray image and, as a result, into any reconstructed volume images.

Scatter can be modeled probabilistically and compensation for scatter can be applied in the same manner, helping to reduce the effects of scatter on the image content that is acquired. Scatter from the scanned subject can be modeled using information about the X-ray source (such as spectral information, filters, and exposure distribution), about detector response, and also about the materials that lie within the irradiated field of view. Thus, scatter compensation can take advantage of information about the anatomy that receives the radiation. In order to more accurately compensate for scatter, it is further useful to provide ways to model scatter that results from interaction of the radiated energy with materials in the volume that lies outside the field of view.

Monte Carlo simulation is a calculation tool that is widely used to model scatter behavior in radiographic imaging. Advantaged over alternate calculation approaches, Monte Carlo techniques have been shown to be useful in helping to solve complex stochastic problems such as radiation scatter, wherein random particle behavior can be evaluated with respect to a probability function. Monte Carlo implementation, however, requires considerable calculation time and resources. Modeling scatter behavior for a conventional 2D radiographic image using Monte Carlo analysis can take a number of hours; this calculation time increases substantially when handling volume 3D images.

Thus, it can be appreciated that methods that streamline the Monte Carlo calculation process can be of considerable value in improving the efficiency of scatter estimation and consequent scatter correction for radiographic images.

SUMMARY

Certain embodiments described herein address the need for a method for estimating and compensating for scatter in radiographic images. Embodiments of the present disclosure provide ways to improve the efficiency of Monte Carlo estimation techniques, particularly for 3D volume images, identifying the subset of the image data that can be used more effectively to model scatter behavior over the full set of image data.

These aspects are given only by way of illustrative example, and such objects may be exemplary of one or more embodiments of the disclosure. Other desirable objectives and advantages inherently achieved by the disclosed disclosure may occur or become apparent to those skilled in the art. The invention is defined by the appended claims.

According to an embodiment of the present disclosure, there is provided a method comprising: a) rotating a radiation source and a detector over a sequence of acquisition angles about a subject and acquiring, at each acquisition angle, a 2D projection image; b) forming a simulation subset that contains some, but not all, of the acquired 2D projection images, wherein subset membership is determined according to relative signal change between successive 2D projection images; c) characterizing scatter for the acquired sequence of projection images according to the formed simulation subset; d) correcting one or more of the acquired sequence of projection images using the scatter characterization; e) reconstructing and storing an image volume according to the sequence of scatter corrected projection images; and f) rendering one or more images of the reconstructed image volume to a display or transmitting the stored image volume data.

According to an alternate embodiment of the present disclosure, there is provided a method for scattered radiation characterization, the method comprising: a) rotating a radiation source and a detector over a sequence of acquisition angles about a subject and acquiring, at each acquisition angle, a 2D projection image; b) forming a simulation subset that contains some, but not all, of the acquired 2D projection images; c) for each projection image in the simulation subset, defining a simulation region for scatter estimation; d) characterizing scatter for the acquired sequence of projection images in the simulation subset according to the defined simulation region; e) correcting the acquired sequence of projection images using the characterized scatter; f) reconstructing and storing a 3D image volume according to the sequence of scatter corrected projection images; and g) rendering one or more images of the reconstructed image volume to a display or transmitting the stored image volume data.

According to another alternate embodiment of the present disclosure, there is provided a method for scattered radiation characterization, the method comprising: a) rotating a radiation source and a detector over a sequence of acquisition angles about a subject and acquiring, at each acquisition angle, a 2D projection image; b) forming a simulation subset for simulation; c) performing a Monte Carlo-type simulation to characterize scatter using the following adjustments: (i) increase the number of photons directed toward low exposure high density regions of the detector; (ii) decrease the number of photons directed toward high-exposure regions of the detector; (iii) adjust photon weighting to reduce bias in scatter estimates; d) compensating for scatter according to the characterization; e) reconstructing and storing an image volume according to the acquired sequence of projection images; and f) rendering one or more images of the reconstructed image volume to a display or transmitting the stored image volume data.

BRIEF DESCRIPTION OF THE DRAWINGS

The foregoing and other objects, features, and advantages of the disclosure will be apparent from the following more particular description of the embodiments of the disclosure, as illustrated in the accompanying drawings. The elements of the drawings are not necessarily to scale relative to each other.

DETAILED DESCRIPTION OF THE EMBODIMENTS

The following is a detailed description of the embodiments of the disclosure, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

In the context of the present disclosure, the term "subject" is used to describe the object that is imaged, such as the "subject patient", "subject hand", or "subject extremity", for example.

In the context of the present disclosure, "volume image content" describes the reconstructed image data for an imaged subject, generally stored as a set of voxels. Image display utilities use the volume image content in order to display features within the volume, selecting specific voxels that represent the volume content for a particular slice or view of the imaged subject. Thus, volume image content is the body of resource information that is obtained from a CT, CBCT, MDCT, tomosynthesis, or other volume imaging reconstruction process and that can be used to generate depth visualizations of the imaged subject. In the context of the present disclosure, the term "volume image" is synonymous with the terms "3 dimensional image" or "3D image".

In the context of the present disclosure, a radiographic projection image, more simply termed a "projection" a "projection image", or an "x-ray image", is a 2D image formed from the projection of x-rays through a subject. In conventional radiography, a single projection image of a subject can be obtained and analyzed. In volume imaging such as CT, MDCT, and CBCT imaging, multiple projection images are obtained in series, then processed to combine information from different perspectives in order to form image voxels.

The term "set", as used herein, refers to a non-empty set, as the concept of a collection of elements or members of a set is widely understood in elementary mathematics. The terms "subset" or "partial subset", unless otherwise explicitly stated, are used herein to refer to a non-empty proper subset, that is, to a subset of the larger set, having one or more members, but not containing every member of the full set. A "proper subset" of set S is strictly contained in set S and excludes at least one member of set S. A "partition of a set" is a grouping of the set's elements into non-empty subsets so that every element is included in one and only one of the subsets. Two sets are "disjoint" when they have no element in common.

In Monte Carlo (MC) simulation, each calculated random variable has an associated variance that is indicative of the relative precision of simulation results. Variance Reduction Techniques (VRT) help to make the simulation more statistically efficient, with greater precision and smaller confidence intervals for the output random variable of interest. Variance reduction is a tool that can be used with Monte Carlo methods to increase estimate precision for a given number of iterations.

By way of reference, Monte Carlo scatter compensation is described, for example, in U.S. Pat. No. 6,256,367 entitled "Monte Carlo Scatter Correction Method for Computed Tomography of General Object Geometries" to Vartanian. Reference is made to an article by Mainegra-Hing and Kawrakow entitled "Variance reduction techniques for fast Monte Carlo CBCT scatter correction calculations" in *Physics in Medicine and Biology*, 55 (2010) pp. 4495-4507.

Reference is further made to an article by Ljungberg, King, Hademenos, and Strand entitled "Comparison of Four Scatter Correction Methods Using Monte Carlo Simulated Source Distributions" in *J. Nucl. Med.* 1994; 35: pp. 143-151. Reference is also made to a dissertation by Ljungberg entitled "Development and Evaluation of Attenuation and Scatter Correction Techniques for SPECT Using the Monte Carlo Method", University of Lund, Sweden, 1990. Further reference is made to an article by Poludniowski, Evans, and Webb entitled "An efficient Monte Carlo-based algorithm for scatter correction in keV cone-beam CT" in *Physics in Medicine and Biology*, 2009 Jun. 21; 54(12): pp. 3847-64.

Figure 1:
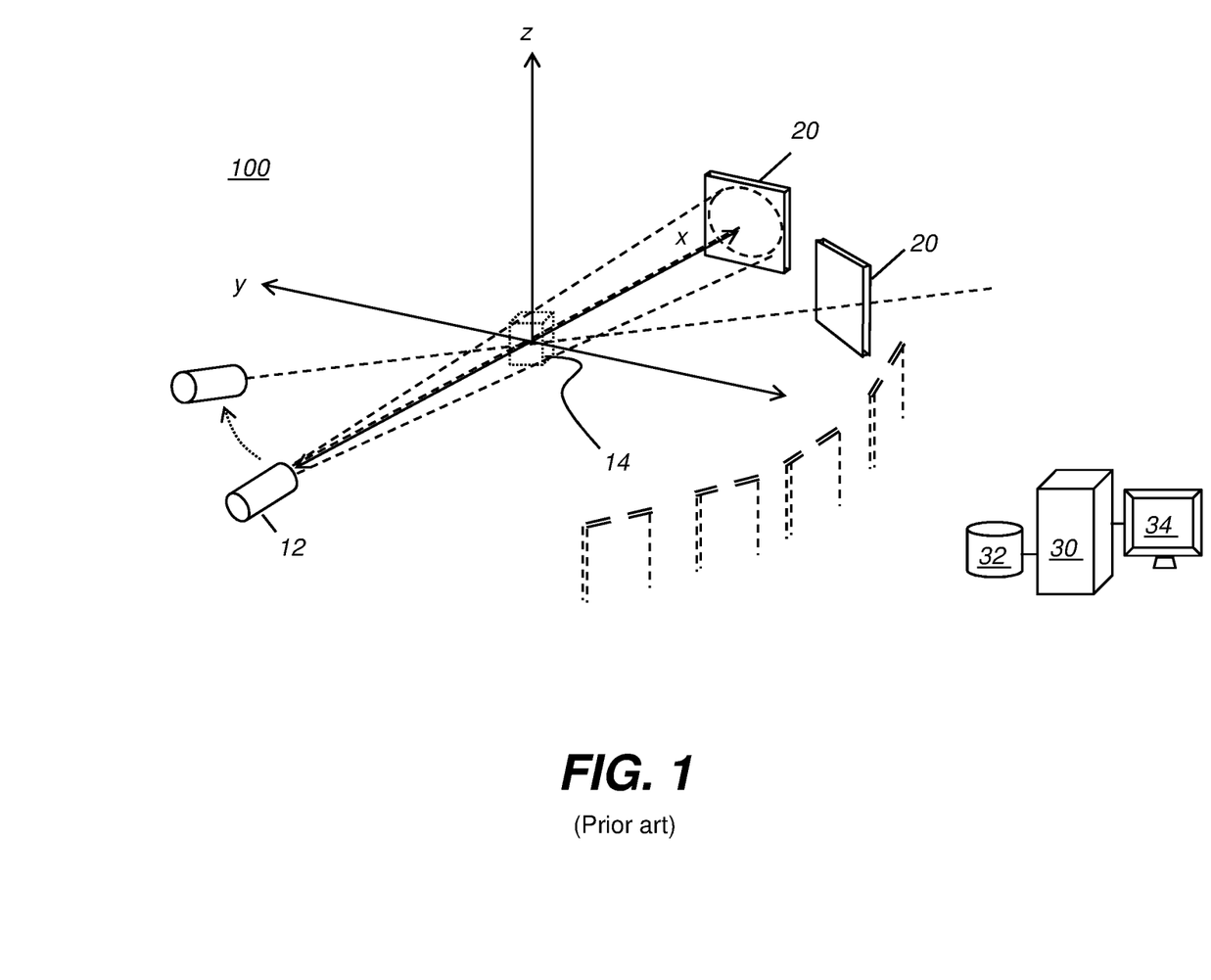
FIG. 1 is a schematic view that shows components of a CBCT image capture and reconstruction system.

In order to more fully understand the methods of the present disclosure and the problems addressed, it is instructive to review principles and terminology used for CBCT image capture and reconstruction. Referring to the perspective view of FIG. 1, there is shown, in schematic form and using enlarged distances for clarity of description, the activity of a conventional CBCT imaging apparatus 100 for obtaining, from a sequence of 2D radiographic projection images, 2D projection data that are used to reconstruct a 3D volume image of an object or volume of interest, also termed a subject 14 in the context of the present disclosure. Cone-beam radiation source 12 directs a cone of radiation toward subject 14, such as a patient or other subject. For a 3D or volume imaging system, the field of view (FOV) of the imaging apparatus is the subject volume that is defined by the portion of the radiation cone or field that impinges on a detector for each projection image. A sequence of projection images of the field of view is obtained in rapid succession at varying angles about the subject, such as one image at each 1-degree angle increment in a 200-degree orbit. X-ray digital radiation (DR) detector 20 is moved to different imaging positions about subject 14 in concert with corresponding movement of radiation source 12. FIG. 1 shows a representative sampling of DR detector 20 positions to illustrate schematically how projection data are obtained relative to the position of subject 14. Once the needed 2D projection images are captured in this sequence, a suitable imaging algorithm, such as filtered back projection (FBP) or other conventional technique, is used for reconstructing the 3D volume image. Image acquisition and program execution are performed by a computer 30 or by a networked group of computers 30 that are in image data communication with DR detector 20. Image processing and storage is performed using a computer-accessible memory 32. Rendered image content from the 3D volume image can be presented on a display 34. Alternately, the 3D volume can be stored or transmitted to another processor.

With respect to the sequence of projection images obtained as shown in FIG. 1, each image is considered to be adjacent to the image just previously acquired and to the very next image acquired in the sequence.

Figure 2:
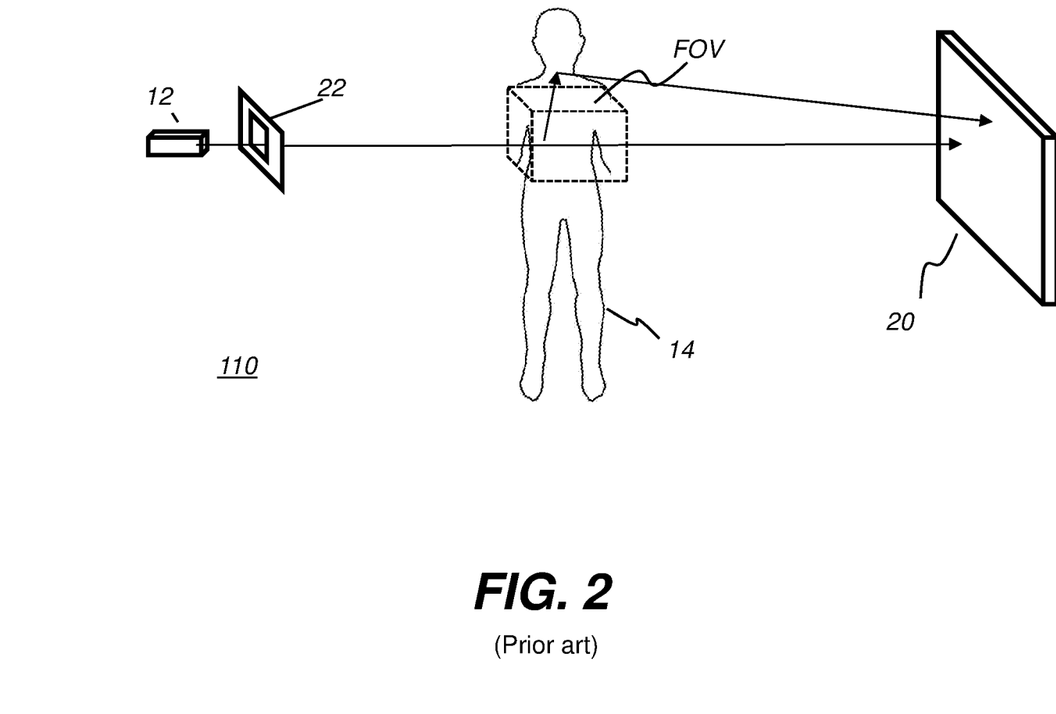
FIG. 2 shows the role of the collimator in constraining radiation and patient dose to the field of view.

As shown in FIG. 2, a collimator 22 of a radiography system 110 provides a widely used tool for reducing patient dose. In operation, the collimator helps to direct the emitted radiation from the x-ray source toward a region or field of view (FOV) of the subject, such as a particular body part, over a limited range of angles. Constraining the estimation of scattered radiation to this FOV tends to underestimate the magnitude of the scattered radiation. Some of the radiation, however, scatters and interacts with material that lies outside the field of view, as shown in FIG. 2. This scattered radiation can contribute to scatter that impinges on detector 20, adding substantial unwanted signal to the detected image content.

Using the volume imaging apparatus of FIG. 1, scatter resulting from radiation within the FOV can be characterized and appropriate compensation can be applied in order to improve the image content, reducing scatter effects without compromising imaging accuracy.

The process for scatter compensation is roughly described by the steps:

(i) characterize the scatter. This can be achieved because internal features within the imaged volume can be suitably identified, along with size, density, and other subject-specific information that can affect scatter characteristics.

(ii) apply appropriate compensation for the scatter information determined in (i).

Embodiments of the present disclosure are directed to methods to step (i). By applying the methods and processes of the present disclosure, an accurate characterization of scatter can be achieved, in a more efficient manner than is provided using conventional scatter estimation methods, dramatically streamlining calculation overhead. Subsequent processing can then apply the needed compensation, in step (ii), and generate and display 2D projection images or slices from the 3-D reconstructed volume of patient anatomy. Although not limited to imaging of particular anatomy, embodiments of the present invention can be of particular utility for CBCT imaging of extremities, such as the human hand, elbow, knee, or ankle.

As noted previously in the background material, Monte Carlo (MC) simulation for volume images, such as CBCT images, can be particularly demanding on computer time and resources. Conventional solutions to alleviate this problem have included using a sampling or partial subset of the projection image data as the basis for computation, then interpolating calculation results to the full data set based on the sampling. This approach selects the subset for sampling using fixed intervals or other criteria. Thus, with reference to FIG. 1 for example, projection images at fixed angular intervals can be used for providing a statistical sampling of the broader data set.

Applicants have recognized that the use of conventional sampling approaches, and the resulting linear interpolation applied to the balance of the image data, often yields less than satisfactory results, particularly with volume image content for more complex anatomy such as extremities and limbs. Embodiments of the present disclosure address the problem of identifying a more suitable subset for Monte Carlo simulation, utilizing information from the projection images themselves.

For CBCT imaging of well-centered symmetric objects, such as for a water calibration phantom, or for anatomy that is not highly complex, scatter does not typically vary widely from one projection image to the next. Sampling processes that form a simulation subset for images of these subjects can thus skip equal numbers of projection images between images selected for scatter characterization and can then characterize scatter for the imaged object with reasonable accuracy.

With complex anatomy, such as a foot, hand, or other limb, however, scatter characterization is more difficult. Between some of the adjacent projection images, there may be very little change in image content; however, between other adjacent projection images, there can be considerable change in image content, and consequently considerable change in scatter. Embodiments of the present disclosure apply an alternate logic to sample selection and reduction of sample size in order to populate a simulation subset that more accurately represents the scatter content of the acquired image content.

Description of Improved Method for Populating the Simulation Subset

According to an embodiment of the present disclosure, a representative subset of the full set of projection images is selected as a simulation subset. In order to vary the sampling rate appropriately for the subject, the criteria for selecting a particular projection image as a member of the subset differs from conventional patterns. Projection images are selected based on the accumulated amount of change in attenuation distribution, with a numerical quantification or score added to a running total of the change from each projection image to the next, adjacent projection image. Where the signal change from one projection image to the next is relatively high, the accumulated value of the score increases at a faster rate. Each time a threshold value is reached, the currently identified candidate projection image is appended to the subset. Processing then continues, correspondingly incrementing the threshold or, alternatively, resetting/updating the threshold for the next accumulated value.

According to an embodiment of the present disclosure, quantification for each projection image $P_i$ uses log exposure. Each log exposure projection image $P_i$ (the i-th log exposure projection image) is obtained and the data processed to quantify the attenuation spatial distribution for that image. Threshold criteria then determine suitability of projection image $P_i$ for selection as a member of the simulation subset, as the image is being processed.

Figure 3:
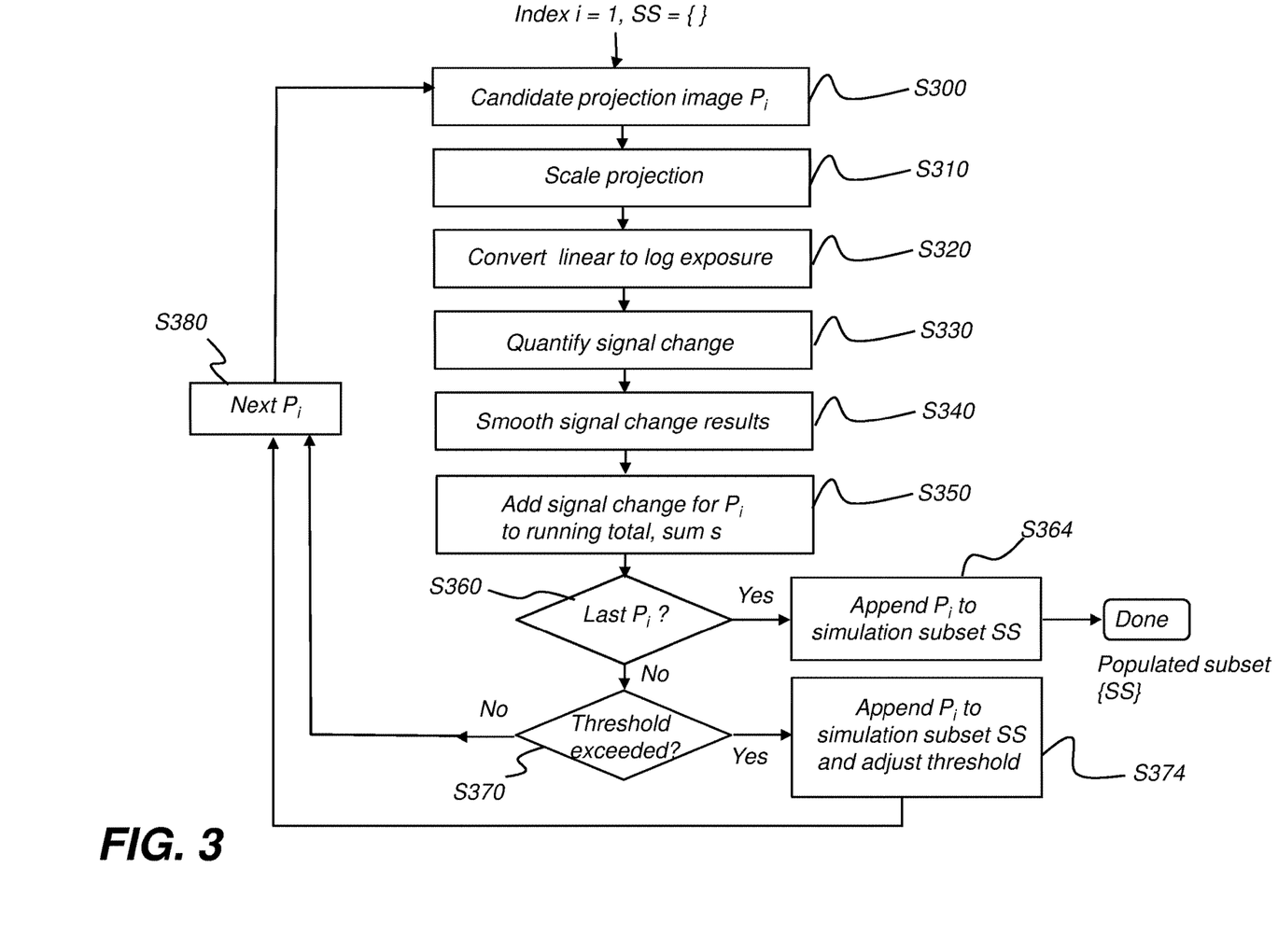
FIG. 3 is a logic flow diagram showing procedural steps for populating the simulation subset.

Processing can use the steps shown in the logic flow diagram of FIG. 3. The simulation subset SS is initially empty. A predetermined threshold $t_k$ is defined: threshold $t_k$=kc (k=0, 1, 2, . . . ), wherein c is a fixed number, e.g., c=22500. The value of threshold $t_k$ can be varied by the user in order to increase the relative resolution where appropriate.

The sequence of FIG. 3 is iterative, checking each projection image that has been acquired for reconstructing a CBCT image, using index i, wherein index i indicates the position of the projection image in an ordered sequence, successively ordered by angle relative to the subject or other reference, or according to acquisition order or timing, and can typically range from 1 to about 200 or more. At initialization of this processing, the simulation subset SS is empty and index i=1:

(1) Candidate identification step S300. In an iterative loop, the processing sequence successively considers each successive projection image as a possible candidate for inclusion in the simulation subset.
(2) Scaling step S310. This step downsizes the identified projection image, such as by a factor of 2 or more in both x and y dimensions. Scaling significantly reduces calculation time for this processing, without noticeably compromising accuracy.
(3) Conversion step S320. The acquired projection image $P_i$ data is typically in the form of linear exposure data. Step S320 converts this data to log exposure data. The candidate projection image is now in the form of a log exposure projection image.
(4) Signal change quantification step S330. This step calculates the total signal change $s_i$ of the identified projection image Pi, relative to the previously obtained image in the series of projection images, such as using:

$$s_i = \sum_{x,y} |P_i(x, y) - P_{i-1}(x, y)|;$$

(5) Smoothing step S340. This step smooths the obtained $s_i$ sequence from step S330 to reduce noise. Smoothing techniques, such as approaches using Gaussian smoothing, low-pass filters, and other smoothing algorithms are well known to those skilled in the image processing arts.
(6) Accumulation step S350. This step adds the smoothed signal change value for $s_i$ to a running total or sum, s.
(7) Looping step S360. This step checks to determine whether or not all projection images P have been processed. If so, an append step S364 appends the candidate projection image $P_i$ to the simulation subset SS and the process terminates.
(8) Interval check step S370. This step compares the running total sum s against the current threshold value $t_k$. Where sum s exceeds $t_k$, an append step S374 adds candidate projection image $P_i$ to the simulation subset SS. The $t_k$ value is updated (value k incremented by the threshold value $t_k$) or, optionally, is reset and processing continues.
(9) Sequencing step S380. This step cycles through the set of projection images to process and add results from the next image $P_i$. In this manner, with each accumulated interval of $t_k$ calculated change, a projection image $P_i$ is appended to the simulation subset SS.

The selected simulation subset can then be processed to characterize scatter for the full image, such as using known Monte Carlo simulation techniques, for example. Scatter characterization can be used to guide scatter compensation, enabling reconstruction of a reduced-scatter 3D volume image from the acquired 2D projection images.

It can be appreciated that variations can be applied to the sequence shown and described with reference to FIG. 3, within the scope of the present disclosure. For example, the first and last projection images $P_1$ and $P_n$ are typically added to simulation subset SS. In addition, other sampling criteria can be applied in order to obtain a more representative simulation subset {SS, for example.

Example 1—Water Phantom

The water phantom is a symmetric object. If the phantom is positioned in the center of the field of view, scatters of all projections are theoretically the same. However, the water phantom can be positioned somewhat off-center. For the successive projection images that are obtained, there is then an approximately constant total signal difference across all projections due to the off-center position.

Figure 4:
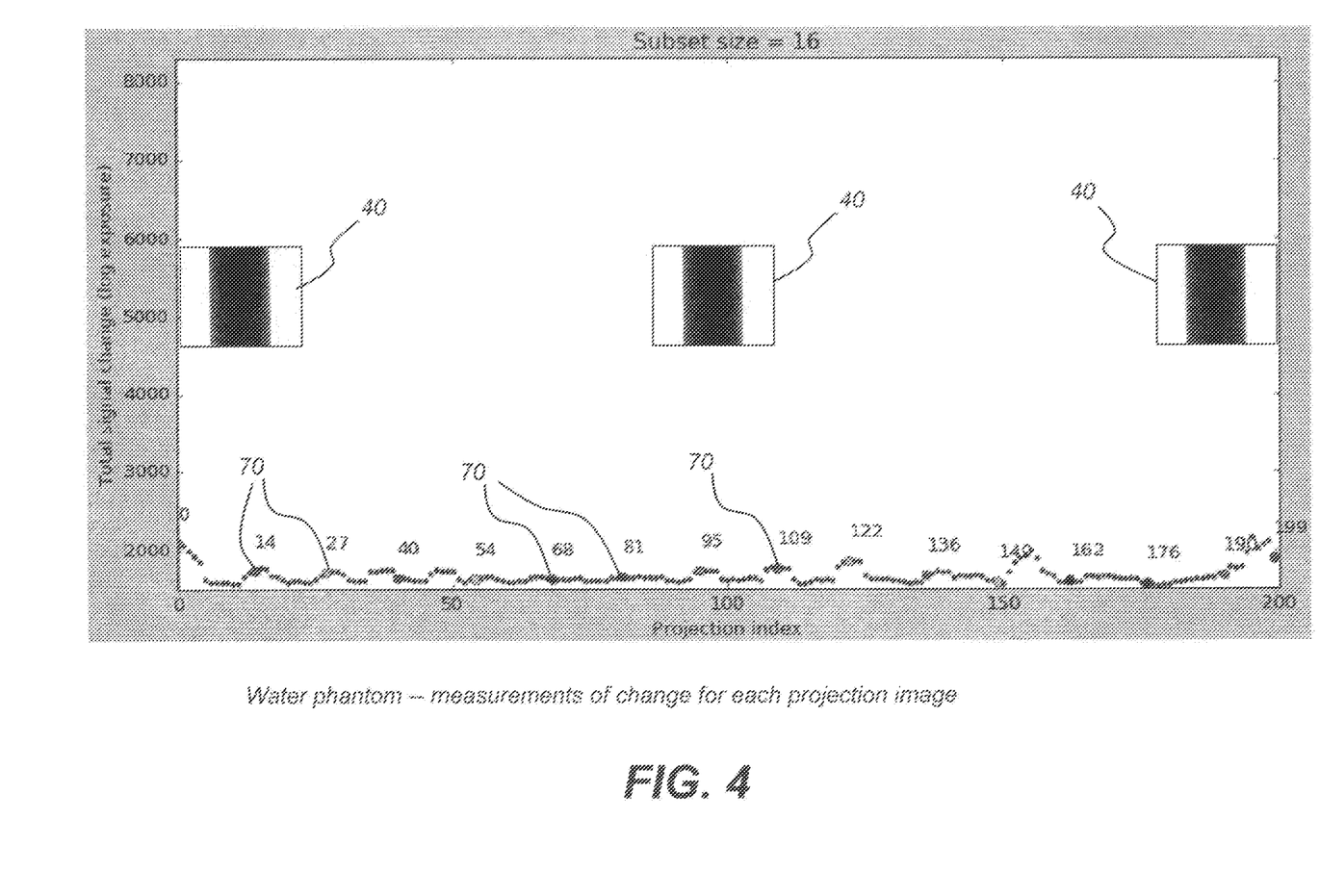
FIG. 4 is a chart that shows results from computing the total signal change for imaging a water phantom and consequent simulation subset selection.

The graph of FIG. 4 shows, for each member log exposure projection of a set of 200 projection images $P_i$, the total change that is calculated, using the calculation method previously described. A small number of representative thumbnail images 40 is shown. As can be seen from this graph, change from one projection image to the next adjacent projection image is relatively small, as expected. Because of the slow change of the total signal difference due to the relative similarity between scatter distributions, 16 projection images are selected as members of the simulation subset {SS} in this example, as indicated by bold dots 70 and corresponding projection numbers in the graph. The simulation subset {SS} for this subject can thus be formed using projection images at the indicated chart positions in the sequence, as shown by numbers {0, 14, 27, 40, . . . }.

Using a conventional, fixed-interval selection method, a larger number of projection images would be selected, typically in the neighborhood of 40 projection images or more. By reducing the number of projection images selected from 40 to 16, there is no compromise in relative scatter calculation accuracy; this type of reduced set can help to accelerate Monte Carlo simulation by a factor of about 3 times.

Example 2—Ankle

Figure 5:
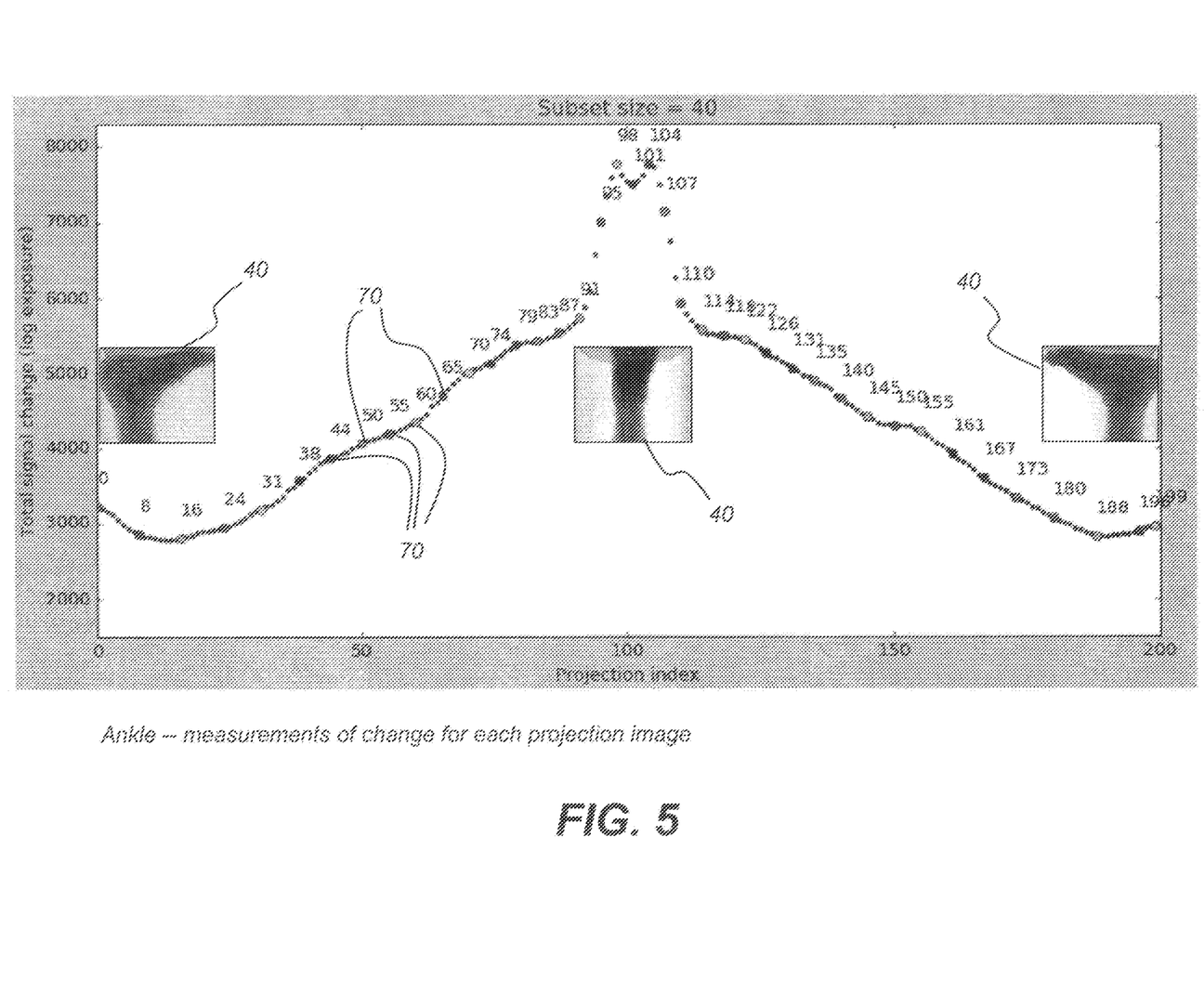
FIG. 5 is a chart that shows results from computing the total signal change for imaging an ankle and consequent simulation subset selection.

Actual patient anatomy is far more complex than the water phantom of FIG. 4, with the amount of change per image varying significantly over the course of 200 projection image scans. The example graph of FIG. 5 shows total change and simulation subset {SS} selection for imaging the human ankle. A small number of thumbnail images 40 is shown.

Using conventional methods to populate the simulation subset {SS}, a fixed interval is used, as described previously, typically selecting 40 projection images Pi at equal intervals. For the 200 member set of projection images Pi, this means that scatter distribution is computed for every 5 projection images, regardless of the relative complexity and amount of change from one projection image to the next.

In the example of FIG. 5, approximately 40 projection images Pi are selected for membership in simulation subset SS; however, the interval between selections varies based on the relative amount of change from one projection image to the next. In FIG. 5, the total signal changes as a function of the accumulated change index. The projection images included in the subset {SS} are similarly shown as in FIG. 4, indicated by bold dots 70 and with corresponding projection numbers in the graph, such as {0, 8, 16, 24, 31, . . . }. Noticeably, the total signal change $s_i$ is relatively small for projection images at the beginning and end of the projection sequence, so that the interval between projection images over this region is about 7 or 8. For projections centering around projection 100, however, such as where the AP/PA view of the ankle changes rapidly from one projection image to the next, this interval between selected projection images decreases dramatically to about 3 or 4. Use of this smaller interval over these scan positions can help to reduce interpolation errors that might otherwise occur if simple averaging techniques were used.

Example 3—Hand

Figure 6:
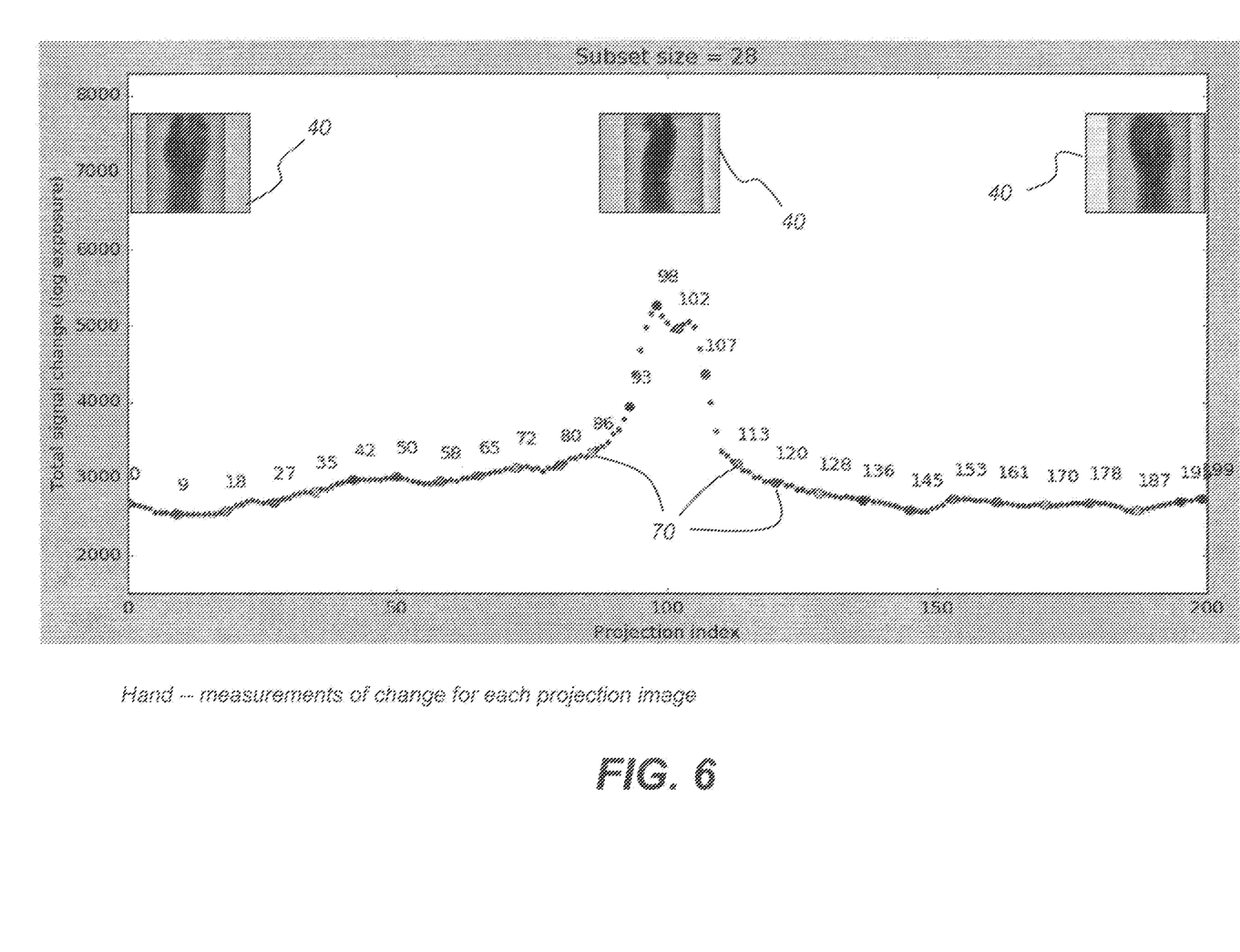
FIG. 6 is a chart that shows results from computing the total signal change for imaging a hand and consequent simulation subset selection.

As another example for showing simulation subset {SS} selection, the graph of FIG. 6 shows total change and subset selection for imaging the human hand. A small number of thumbnail images 40 is shown. Similar to the ankle dataset of FIG. 5, for the AP/PA (A=anterior; P=posterior) views of the hand, the interval between selected projection images $P_i$ is relative large (i.e., about 8 or 9). For the lateral views, the interval decreases to about 4 or 5.

The projection images included in the subset are similarly shown as in FIGS. 4 and 5, indicated by bold dots 70 and corresponding projection numbers in the graph, such as {0, 9, 18, 27, 35, . . . }. The simulation subset {SS} size can be reduced from the conventional selection of 40 images, such as using only 28 projection images due to the relatively small size of the hand.

Limiting the Simulation Region

An embodiment of the present disclosure gains additional benefit for Monte Carlo simulation by limiting the size of a simulation region. In Monte Carlo simulation, photons are emitted from the X-ray source to the detector with equivalent probability, and the photons move through the volume with the same step length (determined by the Woodcock method, for example). If, along the photon path, there is only air or other relatively low density material, computation time and resources can be wasted, because negligible scatter is generated for low density content. The Applicants have found that, by careful identification of the simulation region and by skipping low density regions of the volume in scatter calculation, simulation speed can be significantly accelerated, without perceptible detriment to scatter simulation results.

Figure 7A:
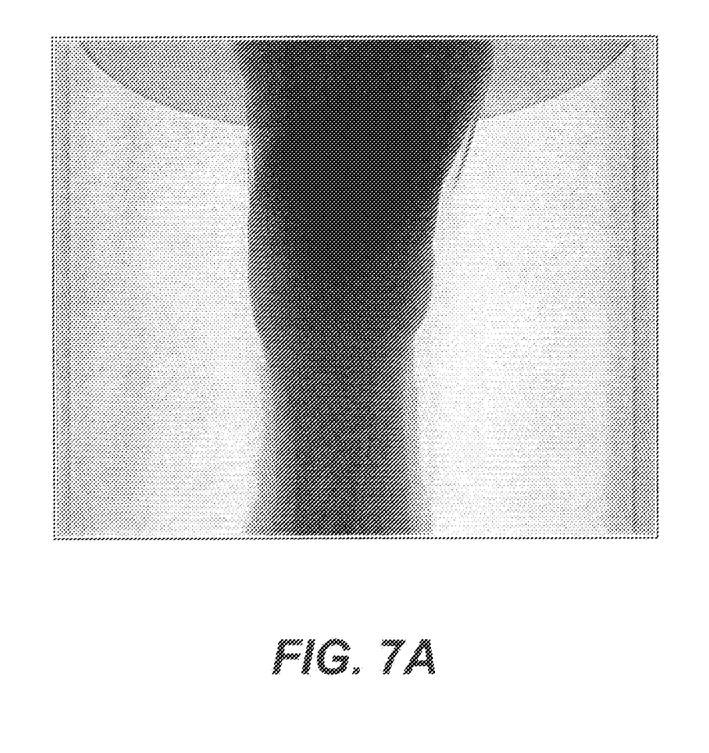
FIG. 7A shows a representative projection image for ankle imaging.
Figure 7B:
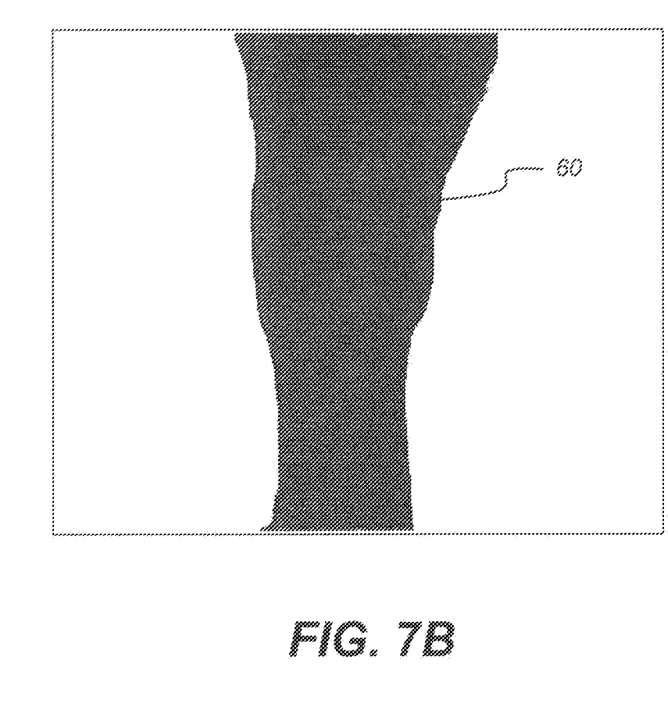
FIG. 7B shows selection of a simulation region for the image of FIG. 7A.

Defining and using a suitable simulation region using the projection information can be accomplished using the following steps:

(i) As shown in the example of FIGS. 7A and 7B, select a threshold to segment the low exposure region of the detector as the simulation region. FIG. 7A shows an exemplary projection image from an ankle dataset. FIG. 7B highlights the segmented region of the detector identified as a simulation region 60 for this purpose. It should be noted that segmentation using a threshold value is one straightforward method for defining the region of interest (ROI) for scatter simulation processing; other more complex segmentation methods can be employed. For complex structures such as extremities, other segmentation methods may be more advantageous than simple thresholding.

(ii) During the Monte Carlo simulation, check whether the photon points to the identified simulation region. If yes, continue the normal simulation; otherwise, ignore this direction, and generate a new direction for photon movement.

This method thus considers photon energy incident on the region of interest and ignores photon energy directed outside this region. Using this technique, the Monte Carlo simulation process for an ankle image can be reduced by about 66%, yielding a simulation speed that is about 3 times faster than that provided using conventional Monte Carlo simulation.

The Applicants have determined that this method, by using a well-defined simulation region, can be particularly effective for smaller objects, such as the ankle, arm, and hand. If more highly radio-opaque equipment components, such as an equipment surface, access door, or padding materials, are included in the projection images, they can be ignored for the first several MBIR (statistical model based iterative reconstruction) iterations in order to allow faster simulation speed. These ignored portions can then be re-considered in the final reconstruction iterations for improved accuracy. For example, various segmentation methods, such as threshold-value based segmentation, can be used to identify highly opaque materials that are not part of the imaged subject and thus can be removed from iterative computation.

The method of limiting the simulation region can be applied to all members of the simulation subset {SS} regardless of subset selection criteria, whether member projection images are selected at equal intervals using conventional selection methods or selected according to accumulated signal change from one image to the next, as described previously in the present disclosure.

Determining Suitable Angular Dependent Photon Distribution for Simulation

In conventional Monte Carlo simulation, photons are emitted from the X-ray source toward the detector with equal angular probability. In directions having dense body tissues along the photon paths, most of the photons will be scattered. Thus, there are fewer photons available for interaction deeper in the scanned body part. This localized effect can cause significant variation in the estimated scatter distribution. In order to compensate for this effect, the Applicants have found an advantageous approach that employs angular dependent photon distribution.

To implement an angular dependent photon distribution, the following steps can be used in simulation processing:
  (i) Increase the number of photons directed to low exposure locations that correspond to high density subject content (for example, to bone features);
  (ii) Reduce the number of photons directed to high exposure locations that correspond to low density subject content (for example, to skin and fatty tissue anatomy);
  (iii) To reduce induced bias to the estimated scatter, adjust the weight of each photon accordingly.

Figure 8:
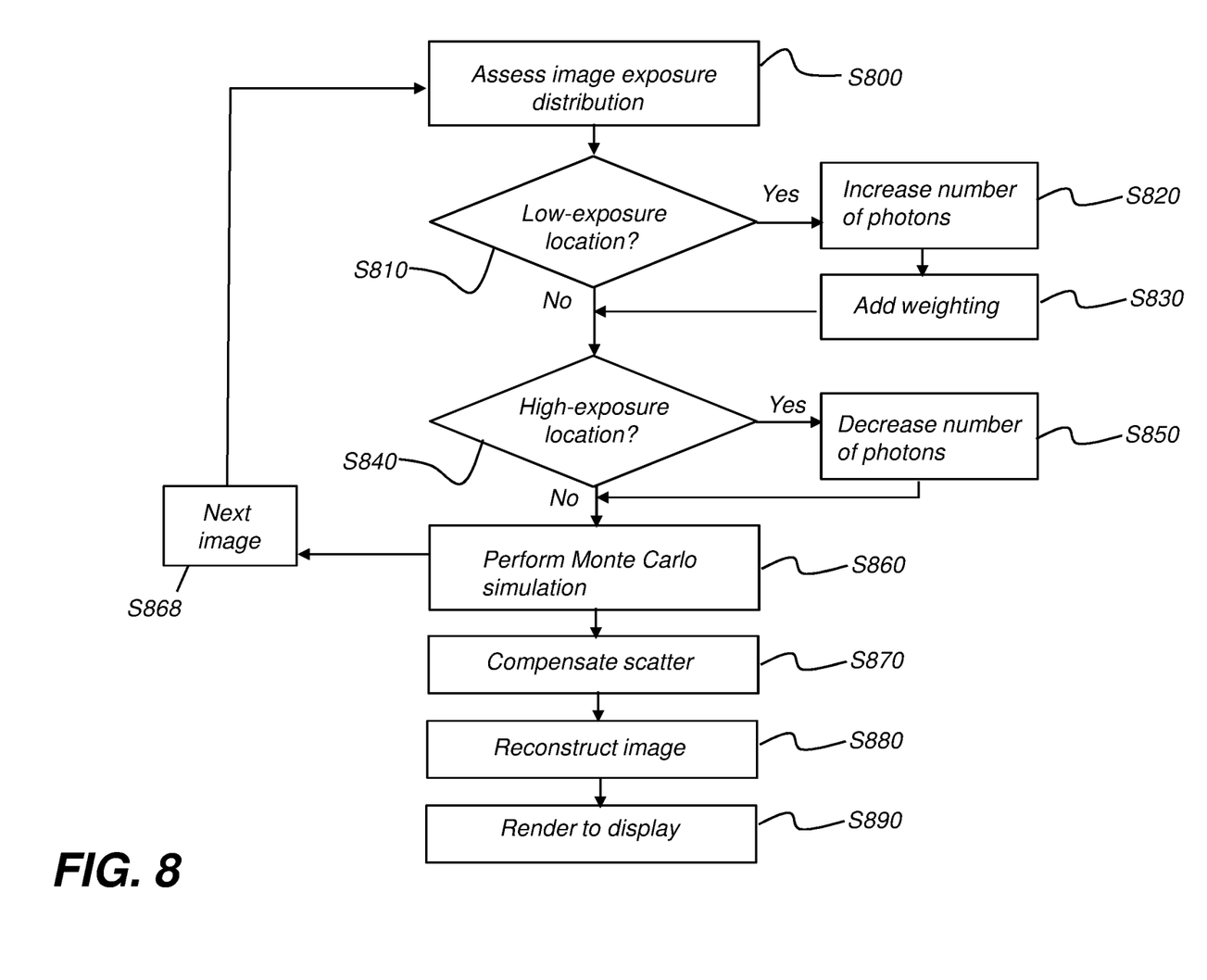
FIG. 8 is a logic flow diagram that shows steps for simulation processing using angular dependent photon distribution according to an embodiment of the present disclosure.

The logic flow sequence shown in FIG. 8 shows steps for simulation processing using angular dependent photon distribution according to an embodiment of the present disclosure. Following image acquisition and the optional process of forming a simulation subset, an assessment step S800 analyzes image content to characterize the image exposure distribution. A first decision step S810 identifies areas of low exposure. Where these are identified, an increase photons step S820 increases the number of photons directed toward corresponding low exposure, high-density regions of the detector. A weighting step S830 adjusts weighting of these added photons. A second decision step S840 identifies areas of high exposure, low density. A decrease photons step S850 decreases the number of photons directed thereto. A simulation step S860 then executes Monte Carlo simulation using the adjusted parameters. A looping step S868 then selects the next image from the simulation subset. When all of the projection images have been processed, a compensation step S870 then performs the needed scatter compensation on the complete set of projection images according to the simulation results. A reconstruction step S880 executes, forming the 3D image using the compensated projection images. A rendering step S890 then renders one or more reconstructed image views to the display. The 3D volume and any rendered images can alternately be stored or transmitted to another system for further processing.

The default value that is assigned for photon weight is 1. For photons in directions that extend through high attenuation materials, the scatter signals are generally very low, and the corresponding scatter image very noisy. To overcome this problem, an embodiment increases the photon number by a multiple of an integer N in order to boost the scatter signals. At the same time, in order to avoid inducing bias or to neutralize the extra photons, the weight assigned to each photon can be reduced, such as to 1/N. The value of integer N can be empirically determined. The total accumulation of weight values can thus be effectively "normalized" using this weighting method.

The concept of 'weight' can be illustrated by considering a photon counting detector in each of the following cases:
  (1) Situation 1: A single photon with assigned weight 1 yields 1 signal;
  (2) Situation 2: A number of photons N, each assigned weight 1/N, also yields 1 signal.

In terms of impact on Monte Carlo logic, the above two situations can be considered to be essentially equivalent. However, the $2^{nd}$ situation, while it does increase the overall simulation time by a factor of N, can yield a more acceptable smoothing image (or scatter image).

It can be appreciated that the different methods described herein for optimizing the simulation subset, limiting the simulation region, and adjusting the photon distribution, can be used independently from one another or in combination. Other processing sequences for improving scatter simulation can alternately be executed in conjunction with the methods described herein.

Methods for scatter characterization are well known to those skilled in the radiographic imaging arts. Using the teaching of the present disclosure, scatter can be simulated and characterized using the simulation subset of projection images that is formed. Alternately, or in conjunction with this method, scatter characterization can use a limited simulation region for its calculations. Further, either separately or in addition to limiting the subset or simulation region, angular dependent photon distribution can be used as a factor in scatter simulation and compensation.

Scatter compensation can be calculated using the derived characterization and one or more of the acquired sequence of projection images can be compensated for scatter using the scatter characterization. A volume image can then be reconstructed from the scatter corrected projection images and rendered to a display, transmitted, or stored as needed.

Reference is made to US 2008/0095302 (Ruhrnschopf) and WO 2016/003957 (Lin), both of which are incorporated herein in their entirety.

Reconstruction techniques can include well known reconstruction algorithms such as filtered back projection (FBP), FDK (Feldkamp, Davis, Kress) processing, or algebraic reconstruction methods, for example.

Consistent with at least one embodiment, the present disclosure utilizes a computer program with stored instructions that control system functions for image acquisition and image data processing for image data that is stored and accessed from an electronic memory. As can be appreciated by those skilled in the image processing arts, a computer program of an embodiment of the present disclosure can be utilized by a suitable, general-purpose computer system, such as a personal computer or workstation that acts as an image processor, when provided with a suitable software program so that the processor operates to acquire, process, transmit, store, and display data as described herein. Many other types of computer systems architectures can be used to execute the computer program of the present disclosure, including an arrangement of networked processors, for example.

The computer program for performing the method of the present disclosure may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present disclosure may also be stored on computer readable storage medium that is connected to the image processor by way of the internet or other network or communication medium. Those skilled in the image data processing arts will further readily recognize that the equivalent of such a computer program product may also be constructed in hardware.

It is noted that the term "memory", equivalent to "computer-accessible memory" in the context of the present disclosure, can refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It is understood that the computer program product of the present disclosure may make use of various image manipulation algorithms and processes that are well known. It will be further understood that the computer program product embodiment of the present disclosure may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present disclosure, are not specifically shown or described herein and may be selected from such algorithms, systems, hardware, components and elements known in the art.

The disclosure has been described in detail, and may have been described with particular reference to a suitable or presently preferred embodiment, but it will be understood that variations and modifications can be effected within the spirit and scope of the disclosure. The presently disclosed embodiments are therefore considered in all respects to be illustrative and not restrictive. The scope of the disclosure is indicated by the appended claims, and all changes that come within the meaning and range of equivalents thereof are intended to be embraced therein.

What is claimed is:

1. A method comprising:
DA accessing a sequence of 2D projection images of a subject acquired over a plurality of acquisition angles;
forming a simulation subset that includes some, but not all, of the 2D projection images, including:
determining the simulation subset according to an accumulated relative signal change between successive 2D projection images;
identifying one of the 2D projection images as a candidate projection image;
calculating a change value according to a relative signal change between the candidate projection image and an adjacent projection image immediately before or after the candidate projection image;
adding the calculated change value to an accumulated sum;
comparing the accumulated sum to a predetermined threshold value; and
if the threshold value is exceeded, assigning the candidate projection image to the simulation subset and incrementing the threshold value by a predetermined increment;
characterizing scatter for the sequence of projection images according to the formed simulation subset;
correcting one or more of the sequence of 2D projection images using the scatter characterization;
reconstructing and storing an image volume according to the sequence of scatter corrected projection images; and
rendering one or more images of the reconstructed image volume to a display or transmitting the stored image volume data.

2. The method of claim 1, further comprising preprocessing the candidate projection image by scaling to reduced resolution.

3. The method of claim 1, further comprising preprocessing the candidate projection image by converting the candidate projection image to log-exposure data form.

4. The method of claim 1, further comprising smoothing the calculated change value.

5. The method of claim 4, wherein smoothing is accomplished by applying Gaussian smoothing logic.

6. The method of claim 1, further comprising identifying a simulation region within 2D projection images in the simulation subset.

7. The method of claim 1, wherein characterizing scatter comprises performing a Monte Carlo-type simulation using the following adjustments:
increasing a first number of photons directed toward high density regions;
decreasing a second number of photons directed toward low density regions; and
adjusting photon weighting to reduce bias in scatter estimates.

8. The method of claim 1, wherein the sequence of 2D projection images is acquired by rotating a radiation source and a detector over a sequence of acquisition angles about the subject to acquire, at each acquisition angle, a 2D projection image.

9. A method for scattered radiation characterization, comprising:
a) rotating a radiation source and a detector over a sequence of acquisition angles about a subject and acquiring, at each acquisition angle, a 2D projection image;
b) forming a simulation subset including some, but not all, of the acquired 2D projection images by successive iterations of a sequential selection process comprising:
(i) identifying one of the acquired 2D projection images as a candidate projection image;
(ii) calculating a change value according to a relative signal change between the candidate projection image and an adjacent 2D projection image acquired immediately before or after the candidate projection image;
(iii) adding the calculated change value to an accumulated sum;
(iv) comparing the accumulated sum to a predetermined threshold value; and
(v) if the threshold value is exceeded, assigning the candidate projection image to the simulation subset; and updating the threshold value;
c) characterizing scatter for the acquired sequence of projection images according to the formed simulation subset;
d) correcting one or more of the acquired sequence of 2D projection images using the scatter characterization;
e) reconstructing and storing an image volume according to the sequence of scatter corrected projection images; and
f) rendering one or more images of the reconstructed image volume to a display or transmitting the stored image volume data.

10. The method of claim 9, wherein characterizing scatter comprises performing a Monte Carlo-type simulation.

11. The method of claim 9, further comprising preprocessing the candidate projection image by scaling to reduced resolution.

12. The method of claim 9, further comprising preprocessing the candidate projection image by converting the candidate projection image to log-exposure data form.

13. The method of claim 9, further comprising smoothing the calculated change value.

14. The method of claim 13, wherein smoothing is accomplished by applying Gaussian smoothing logic.

15. The method of claim 9, further comprising identifying a simulation region within 2D projection images in the simulation subset.

16. The method of claim 9, wherein characterizing scatter comprises performing a Monte Carlo-type simulation using the following adjustments:
   increasing a first number of photons directed toward high density regions;
   decreasing a second number of photons directed toward low density regions; and
   adjusting photon weighting to reduce bias in scatter estimates.

17. The method of claim 9, wherein the sequence of 2D projection images is acquired by rotating a radiation source and a detector over a sequence of acquisition angles about the subject to acquire, at each acquisition angle, a 2D projection image.

18. A method for scattered radiation characterization, the method comprising:
   receiving a sequence of 2D projection images of a subject acquired over a plurality of projection angles;
   forming a simulation subset that includes some, but not all, of the received 2D projection images based on measured signal level changes as between successively acquired ones of the 2D projection images;
   for each 2D projection image in the simulation subset, defining a simulation region on the radiation detector for x-ray scatter estimation, including identifying a region on the radiation detector as a low exposure region based on exposure values of the low exposure region satisfying a preset exposure threshold and defining the simulation region as the low exposure region;
   characterizing x-ray scatter for the received sequence of 2D projection images in the simulation subset using simulated x-ray scatter impinging the defined simulation region and ignoring simulated x-ray scatter impinging areas outside the defined simulation region;
   correcting the received sequence of 2D projection images using the characterized scatter; and
   reconstructing a 3D image volume according to the sequence of scatter corrected projection images.

19. The method of claim 18, wherein the step of characterizing x-ray scatter comprises executing Monte Carlo simulation for photon energy incident on the defined simulation region and ignoring photon energy directed outside the simulation region.

20. The method of claim 18, further comprising receiving a sequence of 2D projection images of a human hand, elbow, knee, or ankle acquired over the plurality of acquisition angles.

* * * * *

UNITED STATES PATENT AND TRADEMARK OFFICE
CERTIFICATE OF CORRECTION

PATENT NO. : 10,758,201 B2  
APPLICATION NO. : 16/106718  
DATED : September 1, 2020  
INVENTOR(S) : Yuan Lin et al.

Page 1 of 1

It is certified that error appears in the above-identified patent and that said Letters Patent is hereby corrected as shown below:

In the Claims

Column 13, Line 43, Claim 1     Please replace "A method comprising:  
DA accessing a sequence of 2D projection images of a  
subject acquired over a plurality of acquisition angles;"

With -- A method comprising:  
accessing a sequence of 2D projection images of a subject  
acquired over a plurality of acquisition angles; --

Signed and Sealed this  
Twentieth Day of October, 2020

Andrei Iancu  
*Director of the United States Patent and Trademark Office*